United States Patent
Hauck

(10) Patent No.: US 8,333,705 B2
(45) Date of Patent: *Dec. 18, 2012

(54) SYSTEM AND METHOD FOR NAVIGATING AN ULTRASOUND CATHETER TO IMAGE A BEATING HEART

(75) Inventor: John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/878,545

(22) Filed: Sep. 9, 2010

(65) Prior Publication Data

US 2011/0009740 A1    Jan. 13, 2011

Related U.S. Application Data

(63) Continuation of application No. 11/044,344, filed on Jan. 27, 2005, now Pat. No. 7,806,829, and a continuation-in-part of application No. 10/819,027, filed on Apr. 6, 2004, now Pat. No. 7,263,397, and a continuation-in-part of application No. 09/107,371, filed on Jun. 30, 1998, now Pat. No. 7,670,297.

(60) Provisional application No. 60/539,540, filed on Jan. 27, 2004, provisional application No. 60/461,004, filed on Apr. 7, 2003.

(51) Int. Cl.
*A61B 5/05* (2006.01)
*A61B 8/14* (2006.01)

(52) U.S. Cl. .................. 600/466; 600/424; 600/463

(58) Field of Classification Search .................. 600/463, 600/424, 466
See application file for complete search history.

(56) References Cited

U.S. PATENT DOCUMENTS

| | | |
|---|---|---|
| 3,954,098 A | 5/1976 | Dick et al. |
| 4,173,228 A | 11/1979 | Van Steenwyk et al. |
| 4,304,239 A | 12/1981 | Perlin |
| 4,380,237 A | 4/1983 | Newbower |
| 4,431,005 A | 2/1984 | McCormick |
| 4,444,195 A | 4/1984 | Gold |
| 4,478,223 A | 10/1984 | Allor |
| 4,522,212 A | 6/1985 | Gelinas et al. |
| 4,559,951 A | 12/1985 | Dahl et al. |
| 4,572,186 A | 2/1986 | Gould et al. |
| 4,572,206 A | 2/1986 | Geddes et al. |
| 4,573,473 A | 3/1986 | Hess |
| 4,613,866 A | 9/1986 | Blood |
| 4,628,937 A | 12/1986 | Hess et al. |
| 4,641,649 A | 2/1987 | Walinsky et al. |
| 4,649,924 A | 3/1987 | Taccardi |

(Continued)

OTHER PUBLICATIONS

Fenici, R. R. et al., "Biomagnetically localizable multipurpose catheter and method for MCG guided intracardiac electrophysiology, biopsy and ablation of cardiac arrhythmias", *Int'l Journal of Cardiac Imaging*.

(Continued)

*Primary Examiner* — Long V. Le
*Assistant Examiner* — Helene Bor
(74) *Attorney, Agent, or Firm* — Dykema Gossett PLLC

(57) ABSTRACT

Catheter navigation is coupled with ultrasound imaging to yield a context map showing the location on a heart of the ultrasonically imaged frame.

19 Claims, 6 Drawing Sheets

U.S. PATENT DOCUMENTS

| | | |
|---|---|---|
| 4,660,571 A | 4/1987 | Hess et al. |
| 4,674,518 A | 6/1987 | Salo |
| 4,697,595 A | 10/1987 | Breyer et al. |
| 4,699,147 A | 10/1987 | Chilson et al. |
| 4,706,670 A | 11/1987 | Anderson et al. |
| 4,721,115 A | 1/1988 | Owens |
| 4,777,955 A | 10/1988 | Brayton et al. |
| 4,821,731 A | 4/1989 | Martinelli et al. |
| 4,840,182 A | 6/1989 | Carlson |
| 4,890,623 A | 1/1990 | Cook et al. |
| 4,898,176 A | 2/1990 | Petre |
| 4,898,181 A | 2/1990 | Kessler |
| 4,899,750 A | 2/1990 | Ekwall |
| 4,911,174 A | 3/1990 | Pederson et al. |
| 4,922,912 A | 5/1990 | Watanabe |
| 4,940,064 A | 7/1990 | Desai |
| 4,945,305 A | 7/1990 | Blood |
| 4,945,342 A | 7/1990 | Steinemann |
| 4,951,682 A | 8/1990 | Petre |
| 5,000,190 A | 3/1991 | Petre |
| 5,005,587 A | 4/1991 | Scott |
| 5,025,786 A | 6/1991 | Siegel |
| 5,029,588 A | 7/1991 | Yock et al. |
| 5,042,486 A | 8/1991 | Pfeiler et al. |
| 5,054,492 A | 10/1991 | Scribner et al. |
| 5,054,496 A | 10/1991 | Wen et al. |
| 5,056,517 A | 10/1991 | Fenici |
| 5,058,583 A | 10/1991 | Geddes et al. |
| 5,081,993 A | 1/1992 | Kitney et al. |
| 5,090,411 A | 2/1992 | Higuchi |
| 5,156,151 A | 10/1992 | Imran |
| 5,158,092 A | 10/1992 | Glace |
| 5,161,536 A | 11/1992 | Vilkomerson et al. |
| 5,211,165 A | 5/1993 | Dumoulin et al. |
| 5,220,924 A | 6/1993 | Frazin |
| 5,228,442 A | 7/1993 | Imran |
| 5,237,996 A | 8/1993 | Waldman et al. |
| 5,255,678 A | 10/1993 | Deslauriers et al. |
| 5,255,679 A | 10/1993 | Imran |
| 5,257,629 A | 11/1993 | Kitney et al. |
| 5,273,038 A | 12/1993 | Beavin |
| 5,282,471 A | 2/1994 | Sato |
| 5,295,484 A | 3/1994 | Marcus et al. |
| 5,297,549 A | 3/1994 | Beatty et al. |
| 5,305,745 A | 4/1994 | Zacouto |
| 5,311,866 A | 5/1994 | Kagan et al. |
| 5,323,781 A | 6/1994 | Ideker et al. |
| 5,324,284 A | 6/1994 | Imran |
| 5,325,860 A | 7/1994 | Seward et al. |
| 5,341,807 A | 8/1994 | Nardella |
| 5,345,936 A | 9/1994 | Pomeranz et al. |
| 5,360,006 A | 11/1994 | Geiser et al. |
| 5,372,138 A | 12/1994 | Crowley et al. |
| 5,377,678 A | 1/1995 | Dumoulin et al. |
| 5,385,146 A | 1/1995 | Goldreyer |
| 5,391,199 A | 2/1995 | Ben-Haim |
| 5,397,339 A * | 3/1995 | Desai .......................... 607/116 |
| 5,409,000 A | 4/1995 | Imran |
| 5,411,025 A | 5/1995 | Webster, Jr. |
| 5,433,198 A | 7/1995 | Desai |
| 5,433,729 A | 7/1995 | Adams et al. |
| 5,458,126 A | 10/1995 | Cline et al. |
| 5,551,426 A | 9/1996 | Hummel et al. |
| 5,553,611 A | 9/1996 | Budd et al. |
| 5,558,091 A | 9/1996 | Acker et al. |
| 5,588,432 A | 12/1996 | Crowley et al. |
| 5,601,084 A | 2/1997 | Sheehan et al. |
| 5,622,174 A | 4/1997 | Yamazaki |
| 5,638,819 A * | 6/1997 | Manwaring et al. .......... 600/424 |
| 5,662,108 A | 9/1997 | Budd et al. |
| 5,669,382 A | 9/1997 | Curwen et al. |
| 5,687,737 A | 11/1997 | Branham et al. |
| 5,690,117 A | 11/1997 | Gilbert |
| 5,697,377 A | 12/1997 | Wittkampf |
| 5,701,897 A | 12/1997 | Sano |
| 5,713,363 A | 2/1998 | Seward et al. |
| 5,722,402 A | 3/1998 | Swanson et al. |
| 5,738,096 A | 4/1998 | Ben-Haim |
| 5,797,396 A | 8/1998 | Geiser et al. |
| 5,824,005 A | 10/1998 | Motamedi et al. |
| 5,840,031 A | 11/1998 | Crowley |
| 5,846,198 A | 12/1998 | Killmann |
| 5,848,972 A | 12/1998 | Triedman et al. |
| 5,871,019 A | 2/1999 | Belohlavek |
| 5,908,446 A | 6/1999 | Imran |
| 6,004,269 A | 12/1999 | Crowley et al. |
| 6,095,976 A | 8/2000 | Nachtomy et al. |
| 6,364,835 B1 * | 4/2002 | Hossack et al. ............... 600/443 |
| 6,443,894 B1 | 9/2002 | Sumanaweera et al. |
| 6,603,996 B1 | 8/2003 | Beatty et al. |
| 6,650,927 B1 | 11/2003 | Keidar |
| 6,690,963 B2 | 2/2004 | Ben-Haim et al. |
| 6,923,768 B2 | 8/2005 | Camus et al. |
| 7,270,634 B2 * | 9/2007 | Scampini et al. ............. 600/447 |
| 7,289,843 B2 | 10/2007 | Beatty et al. |
| 2002/0049375 A1 | 4/2002 | Strommer |
| 2003/0093067 A1 | 5/2003 | Panescu |
| 2003/0220541 A1 | 11/2003 | Salisbury et al. |
| 2003/0231789 A1 | 12/2003 | Willis et al. |
| 2004/0006268 A1 | 1/2004 | Gilboa et al. |
| 2004/0193042 A1 | 9/2004 | Scampini et al. |
| 2005/0085718 A1 | 4/2005 | Shahidi |
| 2005/0182319 A1 * | 8/2005 | Glossop ........................ 600/424 |
| 2005/0222554 A1 | 10/2005 | Wallace et al. |
| 2006/0058692 A1 | 3/2006 | Beatty et al. |
| 2006/0079759 A1 | 4/2006 | Vaillant et al. |
| 2006/0084971 A1 | 4/2006 | Beatty et al. |
| 2006/0122514 A1 | 6/2006 | Byrd et al. |
| 2006/0193504 A1 * | 8/2006 | Salgo et al. ................... 382/128 |
| 2006/0270934 A1 | 11/2006 | Savord et al. |

OTHER PUBLICATIONS

Masse, Stephane et al., "A Three-dimensional display for cardiac activation mapping", *Pace*, vol. 14 Apr. 1991.

Wittkampf, Fred H. et al., "New Technique for Real-Time 3-Dimensional localization of regular intracardiac electrodes", *Circulation—Journal of the American Heart Association* Mar. 16, 1999, 1312-1317.

Arisi, G., et al., "Localization of Ectopic Ventricular Focuses By Means of a Diameter Multielectrode Catheter," *Advances in Electrocardiology*, Elsevier Science Publishers B.V. (Biomedical Division), Z. Antaloczy et al., editors, pp. 67-70 (1990).

Branham, B., et al., "A System For Accurate Interactive 3-D Display of Cardiac Electrical Activity," *Computers in Cardiology*, IEEE Computer Society Press 0276-6547/92, pp. 335-338 (Oct. 11-14, 1992).

Breyer, B. and Cikes, I., "Ultrasonically Marked Catheter—A Method For Positive Echographic Catheter Position Identification," *Med. & Biol. Eng. & Comput.*, 22:268-271 (May 1984).

Buckles, D., et al., "Computer-Enhanced Mapping of Activation Sequences in the Surgical Treatment of Supraventricular Arrhythmias," *PACE*, vol. 13, Part I, pp. 1401-1407 (Nov. 1990).

Cikes, I. and Breyer, B., "Complete Cardiac Catheterisation Guided by Ultrasound," *European Heart Journal*, vol. 4 (Suppl. E), p. 21 (1983).

Cikes, I., et al., "Cardiac Catheterisation Guided by Ultrasound," *Journal of the American College of Cardiology*, vol. 3, No. 2, p. 564 (Feb. 1984).

Cikes, I., et al. "Interventional Echocardiography," *Interventional Ultrasound*, 1st Edition, Chapter 25, Munksgaard, Copenhagen, pp. 160-168 (1985).

Cikes, I., "Interventional Echocardiography," *5th Symposium on Echocardiology*, Rotterdam, Abstracts p. 38 (1983).

Cox, J., et al., "Surgery for Atrial Fibrillation," *Cardiac Surgery: State of the Art Reviews*, vol. 4, No. 1, pp. 207-217 (1990).

De Bakker, J., et al., "Endocardial Mapping by Simultaneous Recording of Endocardial Electrograms During Cardiac Surgery for Ventricular Aneurysm," *Journal of American College of Cardiology*, vol. 2, No. 5, pp. 947-53 (Nov. 1983).

Derfus, D. and Pilkington, T., "Assessing the Effect of Uncertainty in Intracavitary Electrode Position on Endocardial Potential Estimates," *IEEE Transactions on Biomedical Engineering*, vol. 39, No. 7, pp. 676-681 (Jul. 1992).

Derfus, D. and Pilkington, T., "Effect of Intracavitary Electrode Position on Endocardial Potential Estimates," *IEEE Engineering in Medicine & Biology Society 10th Annual International Conference*, pp. 185-186 (1988).

Derfus, D., et al., "A Comparison of Measured and Calculated Intracavitary Potentials for Electrical Stimuli in the Exposed Dog Heart," *IEEE Transactions on Biomedical Engineering*, vol. 39, No. 11, pp. 1192-1206 (Nov. 1992).

Derfus, D., et al., "Calculating Intracavitary Potentials From Measured Endocardial Potentials," *Annual International Conference of the IEEE Engineering in Medicine and Biology Society*, vol. 12, No. 2, p. 635 (1990).

Desai, J., et al., "Orthogonal Electrode Catheter Array for Mapping of Endocardial Focal Site of Ventricular Activation," *PACE*, vol. 14, Part I, pp. 557-574 (Apr. 1991).

Downar, E., et al., "Endocardial Mapping of Ventricular Tachycardia in the Intact Human Ventricle: Evidence for Reentrant Mechanisms," *Journal of the American College of Cardiology*, vol. 11, No. 4, pp. 783-91 (Apr. 1988).

Durrer, D. and Van Der Tweel, L., "Spread of Activation in the Left Ventricular Wall of the Dog. II.: Activation Conditions at the Epicardial Surface," *American Heart Journal*, pp. 192-203 (Aug. 1953).

Fann, J., et al., "Endocardial Activation Mapping and Endocardial Pace-Mapping Using a Balloon Apparatus," *Am. J. Cardiol*, vol. 55, pp. 1076-1083 (1985).

Fenici, R. and Melillo, G., "Magnetocardiography: Ventricular Arrhythmias," *European Heart Journal*, vol. 14 (Suppl. E), pp. 53-60 (1993).

Fenici, R., et al. "Catheter Ablation of Cardiac Arrhythmias: Magnetocardiographic Localization of Electrocatheters and Arrhythomagenic Foci," *8th International Congress "The New Frontiers of Arrhythmias*," Marilleva, Italy, pp. 723-731 (Jan. 31-Feb. 6, 1988).

Fenici, R., et al., "Clinical Magnetocardiography: 10 Years Experience at the Catholic University," *International Journal of Cardiac Imaging*, vol. 7, pp. 151-167 (1991).

Harada, A., et al., "Potential Distribution Mapping: New Method for Precise Localization of Intramural Septal Origin of Ventricular Tachycardia," *Circulation*, vol. 78 (Suppl. III), No. 5, pp. III-137-111-147 (Nov. 1988).

Hauer, R., et al., "Endocardial Catheter Mapping: Validation of a Cineradiographic Method for Accurate Localization of Left Ventricular Sites," *Circulation*, vol. 74, No. 4, pp. 862-868 (Oct. 1986).

Hauer, R., et al., "Endocardial Catheter Mapping: Wire Skeleton Technique for Representation of Computer Arrhythmogenic Sites Compared With Intraoperative Mapping," *Circulation*, vol. 74, No. 6, pp. 1346-1354 (Dec. 1986).

Ideker, R., "A Study to Evaluate the Ability of a Multielectrode Intracavitary Probe to Determine the Site of Origin of Ventricular Tachycardia," *Basic Arrhythmia Laboratory, Engineering Research Center in Emerging Cardiovascular Technologies*, Duke University, pp. 1-3.

Ideker, R., et al. "A Computerized Method for the Rapid Display of Ventricular Activation During the Intraoperative Study of Arrhythmias," *Circulation*, vol. 59, No. 3, pp. 449-458 (Mar. 1979).

Ideker, R., et al. "Simultaneous Multichannel Cardiac Mapping Systems," *PACE*, vol. 10, pp. 281-292 (Mar.-Apr. 1987).

Jackman, W., et al., "New Catheter Technique for Recording Left Free-Wall Accessory Atrioventricular Pathway Activation: Identification of Pathway Fiber Orientation," *Circulation*, vol. 78, No. 3, pp. 598-611 (Sep. 1988).

Josephson, M., *Clinical Cardiac Electrophysiology: Techniques and Interpretations*, 2nd ed., pp. 566-580, 608-615, and 770-783 (1993).

Josephson, M., et al., "Comparison of Endocardial Catheter Mapping With Intraoperative Mapping of Ventricular Tachycardia," *Circulation*, vol. 61, No. 2, pp. 395-404 (Feb. 1980).

Josephson, M. et al., "Role of Catheter Mapping in Evaluation of Ventricular Tachycardia," *Ventricular Tachycardia—Mechanisms and Management*, pp. 309-330, Mt. Kisco, NY: Futura Publishing Co. (1982).

Josephson, M., et al. "Role of Catheter Mapping in the Preoperative Evaluation of Ventricular Tachycardia," *American Journal of Cardiology*, vol. 40, pp. 207-220 (Jan. 1982).

Josephson, M., et al. "Ventricular Activation During Venticular Endocardial Pacing, II. Role of Pace-Mapping to Localize Origin of Ventricular Tachycardia," *The American Journal of Cardiology*, vol. 50, pp. 11-22, (Jul. 1982).

Kaltenbrunner, W., et al., "Epicardial and Endocardial Mapping of Ventricular Tachycardia in Patients With Myocardial Infarction: Is the Origin of the Tachycardial Always Subendocardially Localized?," *Circulation*, vol. 84, No. 3, pp. 1058-1071 (Sep. 1991).

Khoury, D. and Rudy, Y., "A Model Study of Volume Conductor Effects on Endocardial and Intracavitary Potentials," *Circulation Research*, vol. 71, No. 3, pp. 511-525 (Sep. 1992).

Khoury, D. and Rudy, Y., "Reconstruction of Endocardial Potentials From Intracavitary Probe Potentials: A Model Study," IEEE 0276-6547/92, pp. 9-12 (1992).

Kun, S. and Peura, R., "Conductance Volumetric Model of an Eccentrically Positioned Catheter Within a Three-Compartment Ellipsoidal Ventricle," *IEEE Transactions on Biomedical Engineering*, vol. 40, No. 6, pp. 589-592 (Jun. 1993).

Langberg, J., et al., "The Echo-Transponder Electrode Catheter: A New Method for Mapping the Left Ventricle," *Journal of the American College of Cardiology*, vol. 12, pp. 218-223 (Jul. 1988).

Laxer, C., et al., "A Graphical Display System for Animating Mapped Cardiac Potentials," *Third Annual IEEE Symposium on Computer-Based Medical Systems*, IEEE Computer Society, pp. 197-204 (1990).

Lu, S and Eiho, S., "Compound 3-D Visualization of Reconstructed Coronary Arteries, Left Ventricle and Aorta From Biplane X-Ray Angiograms," *Computers in Cardiology*, IEEE Computer Society Press, 0276-6547/92, pp. 535-538 (Oct. 11-14, 1992).

Macchi, E., et al., Intracavitary Mapping: An Improved Method for Locating the Site of Origin of Ectopic Ventricular Beats by Means of a Mathematical Model, *IEEE Engineering in Medicine & Biology Society 10th Annual International Conference*, pp. 0187-0188 (1988).

Macchi, E., et al., "Localization of Ventricular Ectopic Beats From Intracavitary Potential Distributions: An Inverse Model in Terms of Sources," *IEEE Engineering in Medicine & Biology Society 11th Annual International Conference*, pp. 0191-0192 (1989).

Mendler, P. et al., "Multichannel Recording of Cardiac Potentials," *Medical and Biological Engineering and Computing*, vol. 18, No. 5, pp. 617-624 (Sep. 1980).

Moshage, W., et al., "Biomagnetic Localization of Ventricular Arrhythmias," *Radiology*, vol. 180, No. 3, pp. 685-692 (Sep. 1991).

Moura, L., et al. "A Microcomputer-Based Cardiac Mapping System for Recurrent Ventricular Tachycardia Surgery," *Computers in Cardiology* IEEE Computer Society Press, 0276-6547/92, pp. 431-434 (Oct. 11-14, 1992).

"New Catheter Will Find and Treat Cardiac Arrhythmias, "WPI Journal, Summer 1993, 2 pages.

Page, P., et al., "Surgical Treatment of Ventricular Tachycardia: Regional Cryoablation Guided by Computerized Epicardial and Endocardial Mapping," *Circulation*, vol. 80 (Suppl. I), No. 3, pp, I-124-I-134 (Sep. 1989).

Pilkington, T., et al., "Feasibility of Estimating Endocardial Potentials From Cavity Potentials," *IEEE Ninth Annual Conference of the Engineering in Medicine and Biology Society*, IEEE, pp. 1875-1876 (1987).

Pogwizd, S. and Corr, P., "Reentrant and Nonreentrant Mechanisms Contribute to Arrhythmogenesis During Early Myocardial Ischemia: Results Using Three-Dimensionial Mapping," *Circulation Research*, vol. 61, No. 3, pp. 352-371 (Sep. 1987).

Pollak, S., et al., "Intraoperative Identification of a Radiofrequency Lesion Allowing Validation of Catheter Mapping of Ventricular Tachycardia With A Computerized Balloon Mapping System," *PACE*, vol. 15, pp. 854-858 (Jun. 1992).

Potratz, J., et al., "Echocardiographic Guiding of Catheter-Electrode During Endocardial Mapping to Determine Location of Late Fractionated Potentials in Patients With Acute Myocardial Infarction," *European Heart Journal*, vol. 12, Abstract Supplement p. 235, abstract 1242 (Aug. 1991).

"Quickhull Algorithm for Convex Hulls," *ACM Transactions on Mathematical Sofware*, vol. 22, No. 4, Dec. 1996, 1 page.

Rudy, Y. and Plonsey, R., "Annotations: A Note on 'The Brody-Effect'," *J. Electrocardiology*, vol. 11, No. 1, pp. 87-90 (1978).

Rudy, Y, and Plonsey, R., "The Eccentric Spheres Model As the Basis for a Study of the Rule of Geometry and Inhomogeneities in Electrocardiography," *IEEE Transactions on Biomedical Engineering*, vol. BME-26, No. 7, pp. 392-399 (Jul. 1979).

Rudy, Y. et al. "Inverse Reconstruction of Epicardial and Endocardial Potentials: The Use of Temporal Information," IEEE, pp. 2006-2008 (1992).

Rudy, Y., et al., "The Effects of Variations in Conductivity and Geometrical Parameters on the Electrocardiogram, Using an Eccentric Spheres Model," *Circulation Research*, vol. 44, No. 1, pp. 104-111 (Jan. 1979).

Simpson, E., et al., "Three-Dimensional Visualization of Electrical Variables in the Ventricular Wall of the Heart," IEEE, TH0311-1/90, pp. 190-194, (1990).

Smith, W. and Ideker, R., "Computer Techniques for Epicardial and Endocardial Mapping," Progress in Cardiovascular Diseases, vol. 26, No. 1, pp. 15-32 (Jul./Aug. 1983).

Smith, W., et al., "A Computer System for the Intraoperative Mapping of Ventricular Arrhythmias," *Computers and Biomedical Research, an International Journal*, vol. 13, No. 1, pp. 61-72 (Feb. 1980).

Spach, M. and Barr, R., "Analysis of Ventricular Activation and Repolarization From Intramural and Epicardial Potential Distributions for Ectopic Beats In The Intact Dog," *Circulation Research*, vol. 37, pp. 830-843 (Dec. 1975).

Spencer, Kirstin Clingman, "A Feasibility Study of Determining The Position of an Intracavitary Multielectrode Probe via Impedance Measurements," *Department of Electrical Engineering in the Graduate School of Duke University*, 1991, pp. i-vii and 1-49.

Stellbrink, C., et al., "Potential of Intercardiac Ultrasonography as an Adjunct for Mapping and Ablation," *American Heart Journal*, vol. 127, No. 4, Part 2, pp. 1095-1101 (Apr. 1994).

Supplementary European Search Report issued in corresponding European Patent Application No. 06 719 666.7 and the European Search Opinion (Jun. 23, 2009).

Taccardi, B., et al., "A New Intracavitary Probe for Detecting the Site of Origin of Ectopic Ventricular Beats During One Cardiac Cycle," *Circulation*, vol. 75, No. 1, pp. 272-281 (Jan. 1987).

Taccardi, B., et al., "Potential Distributions and Excitation Time Maps Recorded With High Spatial Resolution From the Entire Ventricular Surface of Exposed Dog Hearts," *Computers in Cardiology*, IEEE Computer Society Press, 0276-6547/92, pp. 1-4 (Oct. 11-14, 1992).

Tanigawa, M., et al., "Prolonged and Fractionated Right Atrial Electrograms During Sinus Rhythm in Patients With Paroxysmal Atrial Fibrillation and Sick Sinus Node Syndrome," *Journal of the American College of Cardiology*, vol. 17, No. 2, pp. 403-408 (Feb. 1991).

Tweddell, J., et al. "Potential Mapping in Septal Tachycardia: Evaluation of a New Intraoperative Mapping Technique," *Circulation*, vol. 80 (Suppl. I), No. 3, pp. 1-97-1-108 (Sep. 1989).

Witkowski, F. and Corr. P., "An Automated Simultaneous Transmural Cardiac Mapping System," *American Journal of Physiology*, vol. 247, pp. H661-H668 (1984).

Wolf, Patrick Donahoe, "Development and Evaluation of an Algorithm to Determine Boundary Geometry and Electrode Location From Impedance Measurements," *Department of Biomedical Engineering in the Graduate School of Duke University*, 1992, pp. i-viii and 1-86.

Young, M., et al. "A Real-Time Data Acquisition System for the Display of Three Dimensional Cardiac Activation Maps," *Computers in Cardiology*, IEEE Computer Society Press, 0276-6547/92, pp. 331-334 (Oct. 11-14, 1992).

Yuan, S., et al., "Localization of Cardiac Arrhythmias: Conventional Noninvasive Methods," *International Journal of Cardiac Imaging*, vol. 7, pp. 193-205 (1991).

\* cited by examiner

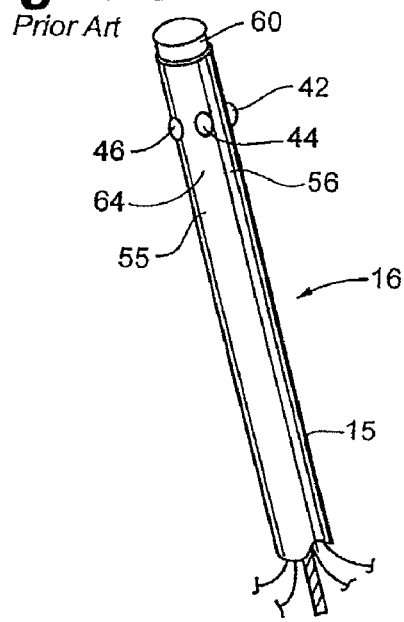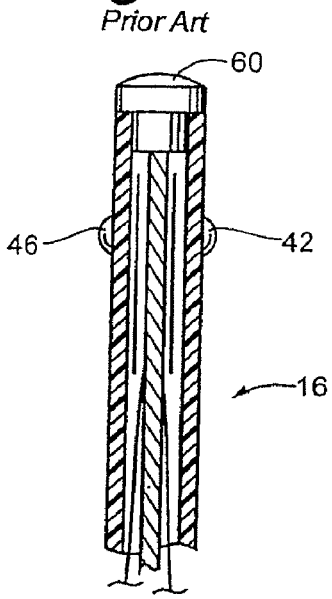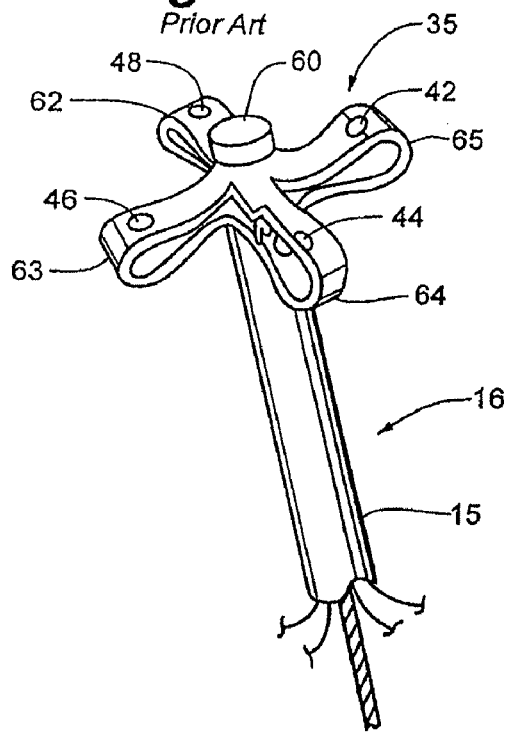

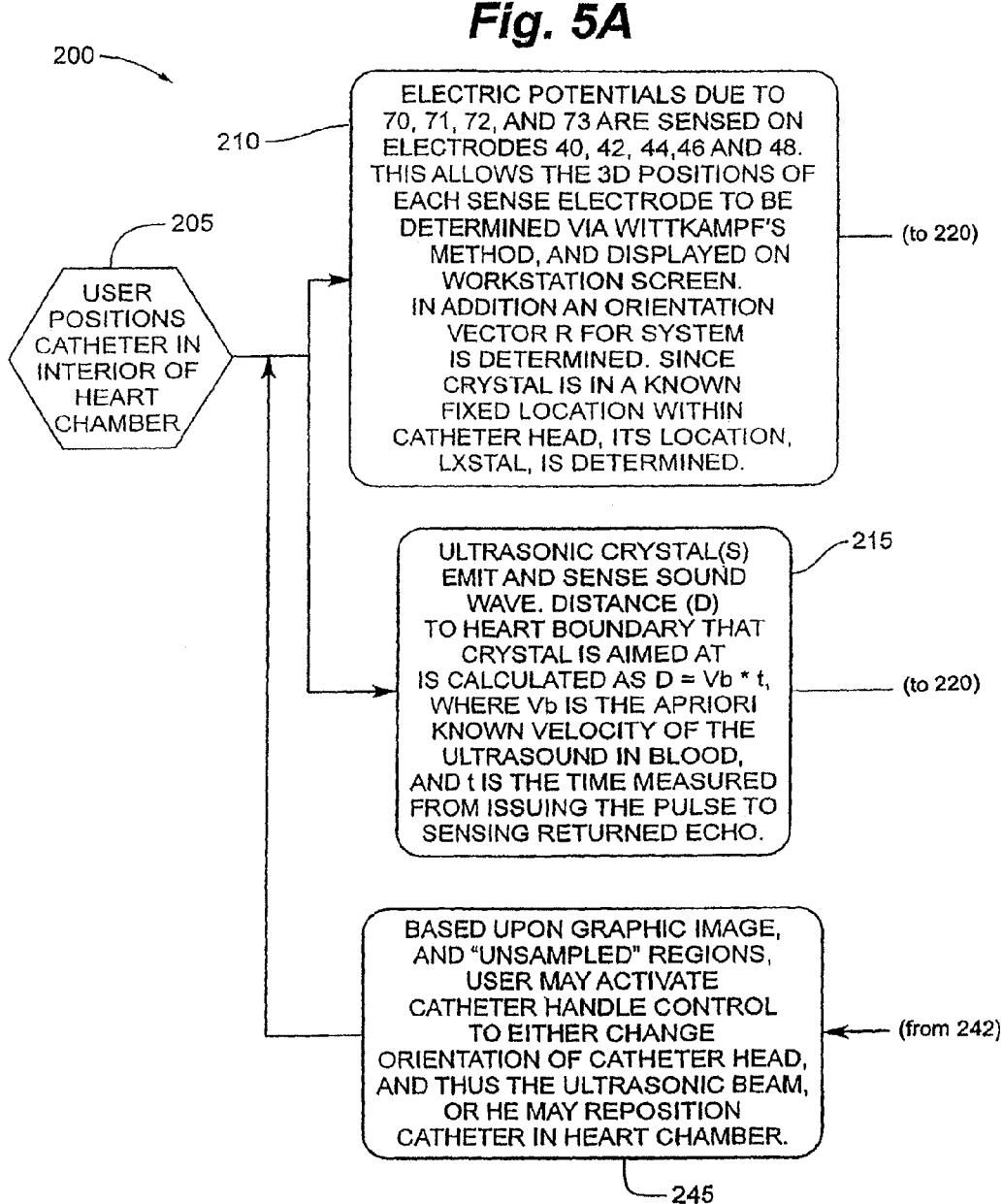

SYSTEM AND METHOD FOR NAVIGATING AN ULTRASOUND CATHETER TO IMAGE A BEATING HEART

The present application is a continuation of U.S. patent application Ser. No. 11/044,344, filed Jan. 27, 2005 which claims the benefit of priority to U.S. Provisional Patent Application No. 60/539,540, filed Jan. 27, 2004 and which is a continuation-in-part of U.S. patent application Ser. No. 10/819,027, filed Apr. 6, 2004, which in turn claims the benefit of priority to U.S. Provisional Patent Application 60/461,004, filed Apr. 7, 2003 and is a continuation in part of U.S. patent application Ser. No. 09/107,371, filed Jun. 30, 1998. Each application referenced in this paragraph is incorporated herein by reference in its entirety.

BACKGROUND OF THE INVENTION a. Field of the Invention

The present invention relates generally to a system and method for navigating an ultrasound catheter to image a beating heart. More particularly, the present invention relates to the coordination of catheter position data with ultrasound imaging data imaging a heart via ultrasound.

b. Background Art

Using ultrasound to image the interior of a beating heart is a known technique. A series of patents (U.S. Pat. No. 5,345,940, issued Sep. 13, 1994; U.S. Pat. No. 6,544,187, issued Apr. 8, 2003; U.S. Pat. No. 5,713,363, issued Feb. 3, 1998) to Seward et al. describe the intra-cardiac ultrasound echo (ICE) technique and are incorporated herein, in their entirety, by reference. According to this technique, an ultrasonic transducer is situated at a distal end of a catheter that is positioned in a heart chamber. The transducer vibrates in response to a control signal to generate an ultrasonic wave. The transducer senses the reflected wave and transmits the corresponding signal to transceiver circuitry that analyzes the incoming signal and generates an image signal that is shown on a display. In this manner, a user can see, on a monitor, a real-time image of a small portion of the interior surface of the heart. Repositioning or reorienting the catheter, such that the transducer's wave bounces off a different portion of the surface, will yield a new image.

The ICE technique has lacked the ability to link the ultrasound information with other clinical information such as cardiac electrographic data anatomic orientation of the ultrasound data or images.

Further, Wittkampf, in a series of patents (U.S. Pat. No. 5,983,126, issued Nov. 9, 1999; U.S. Pat. No. 5,697,377, issued Dec. 16, 1997), describes the application of orthogonal current pulses to an electrode arrangement on a catheter to yield three-dimensional position data to assist a user in navigating the catheter. More specifically, in the Wittkampf system, current pulses are applied to orthogonally placed patch electrodes placed on the surface of the patient. These patches are used to create specific electric fields inside the patient. The Wittkampf patents teach the delivery of small-amplitude low-current pulses supplied continuously at three different frequencies, one on each axis. Any measurement electrode placed in these electric fields experience a voltage that depends on its location between the various patches or surface electrodes on each axis. The voltage on the measurement electrode in the field when referred to a stable positional reference electrode indicates the position of the measurement electrode with respect to that reference. The three voltages give rise to a location of the measurement electrode in "three space".

Co-pending application Ser. No. 10/819,027 describes the application of the Wittkampf technique, with improvements, to locate a catheter positioned in the interior of the heart and to image a catheter in real time. Further, application Ser. No. 10/819,027 describes how to sequentially use locations of an electrode in contact with the heart wall to sequentially build a model of a heart chamber.

Devices and techniques are known for determining the location in space and the orientation of the tip of a catheter. A series of patents to Desai (U.S. Pat. No. 5,215,103, issued Jun. 1, 1993; U.S. Pat. No. 5,231,995, issued Aug. 3, 1993; U.S. Pat. No. 5,397,339, issued Mar. 14, 1995; U.S. Pat. No. 4,940,064, issued Jul. 10, 1990; and U.S. Pat. No. 5,500,011, issued Mar. 19, 1996), incorporated herein by reference in their entirety, describes an electrode array arrangement located on a catheter that can be used to determine the location of the catheter tip using Wittkampfs technique.

What has been needed is a device and method for producing images of the interior of a heart via ultrasound coupled with a navigational system for allowing the user to see what portion of the heart is appearing on the ultrasound image. Further, what has been needed is a method for building a geometry of the heart by successively imaging portions of the heart surface, with successive images being framed based the location of the frames previously taken and by corresponding manipulation of the imaging device to select a new frame.

SUMMARY OF THE INVENTION

An object of the present invention is to provide a convenient, easy-to-use system and method for ultrasonically imaging a desired portion of a beating heart.

Another object of the present invention is to provide a system for identifying, on a context map, the location of an image obtained of an interior surface of a beating heart via ultrasound.

Yet another object of the present invention is to build a model of a heart chamber through sequential ultrasound imaging with collection and calculation of position and orientation data.

Still another object of the present invention is to allow easy updating or elucidation of important heart structure after a working model of the heart is constructed.

Another object of the invention is to build a geometry of a beating heart without touching the endocardial wall with a probe.

Yet another object of the present invention is to provide a system to provide lower cost transseptal puncture procedures using a smaller catheter than is typically used for ICE.

BRIEF DESCRIPTION OF THE DRAWINGS

An exemplary version of a system for navigating an ultrasound transducer is shown in the figures wherein like reference numerals refer to equivalent structure throughout, and wherein:

FIGS. 3a, b, c are prior art depictions of an electrode array that is employed in the system of FIGS. 1 and 2;

DETAILED DESCRIPTION OF EMBODIMENTS OF THE INVENTION

Figure 1:
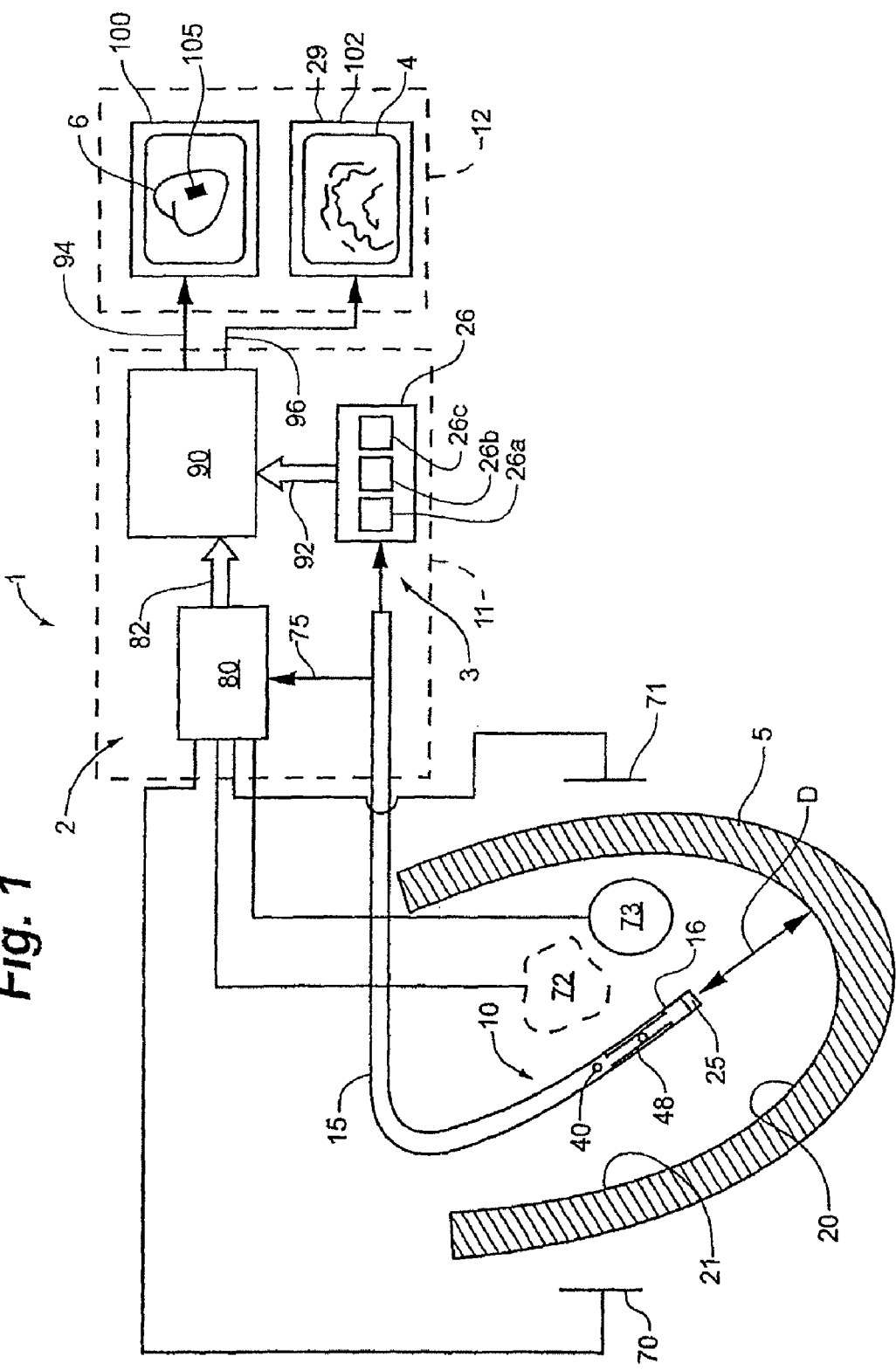
FIG. 1 is a schematic representation of a system for navigating an ultrasound transducer.

FIG. 1 shows a cardiac imaging and navigation system 1 that coordinates an ultrasonic data acquisition and imaging system 2 with a catheter navigation system 3. The system 1 produces an ultrasonic image 4 of the heart 5 and displays a context or reference map 6 of the heart indicating the portion of the heart 5 that appears in the ultrasonic image frame 4. In a preferred use, the system 1 observes a beating heart 5. The navigation system 1 includes a catheter system 10 electronically linked to a signal processing system 11 that in turn is electronically linked to an image display system 12. In one embodiment, these electronic linkages are made via wire connections. In other embodiments, wireless links may be used for data transfer.

Figure 2:
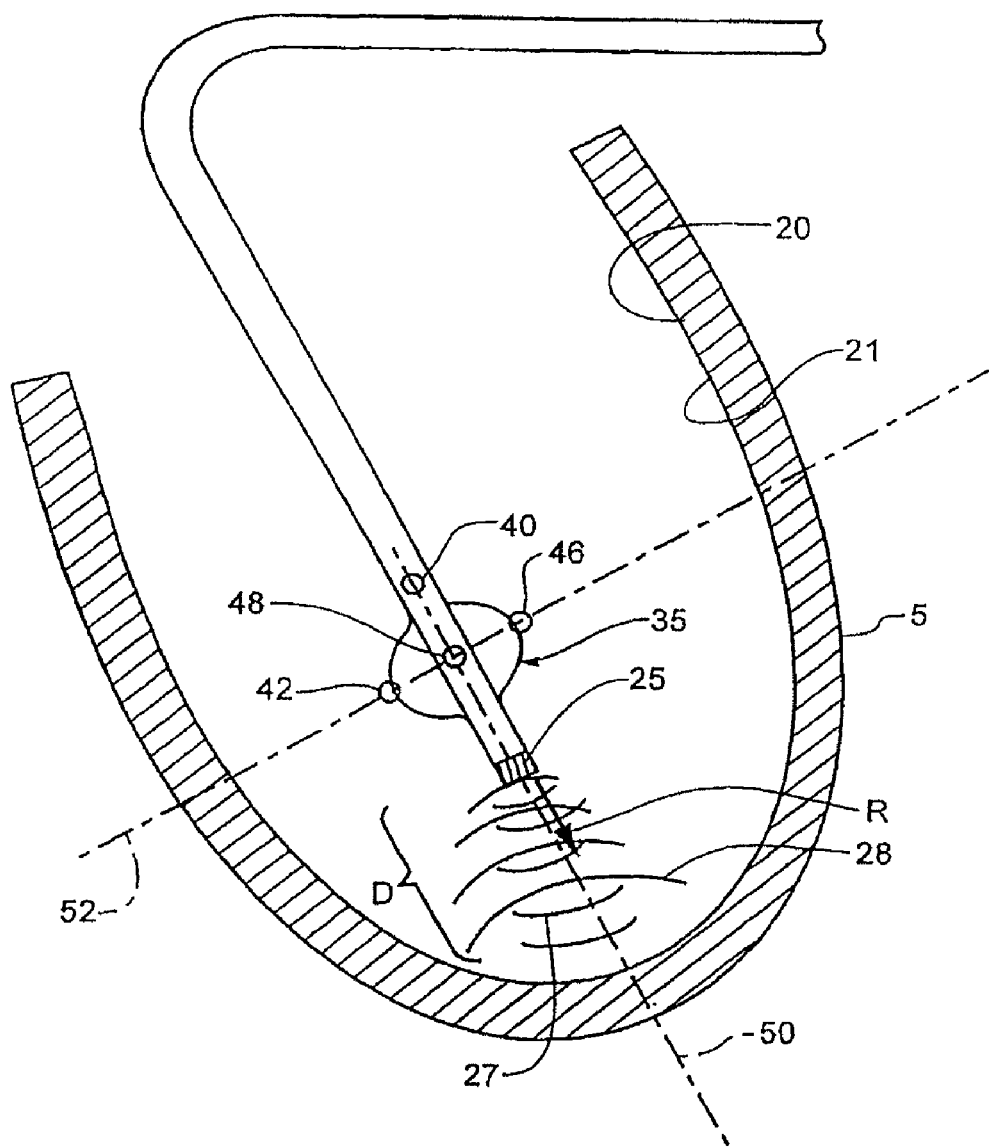
FIG. 2 is a partial view of the system of FIG. 1, with an electrode array in a deployed configuration and with ultrasound waves and echos depicted.

A preferred catheter system 10 is illustrated in FIGS. 1 and 2. The catheter system 10 includes a guide tube 15 that is somewhat flexible so that in use it can easily pass through a patient's cardiovascular structures. In use, the catheter's distal end or tip 16 can be positioned within a heart chamber 20 defined by a chamber wall 21, as shown in FIGS. 1 and 2.

Proximate the distal end 16 of the catheter system 10, is an ultrasonic transducer 25 that includes a crystal or array of crystals for sending and sensing ultrasonic waves. The transducer 25 is electronically linked to a dedicated ultrasound processor 26 having or linked to transceiver circuitry 26a, control circuitry 26b and imaging circuitry 26c. Via the transceiver 26a, the ultrasound processor 26 triggers a vibration in the ultrasonic transducer 25 that in turn imparts an sound wave 27 (FIG. 2) to the surrounding blood in the heart chamber 20. The wave 27 propagates through the blood in a direction determined or calculable from the known position and orientation of the crystals in the transducer 25. The wave 27 "bounces" against the chamber wall 20. A portion 28 of the wave 27 is reflected by the chamber wall 20 and returns to the transducer 25. The transducer 25 senses the returned wave 28 and sends a signal to the ultrasound processor 26. The ultrasound processor 26 has data storage and processing functions that calculate the distance "D" between the transducer and the heart wall 21, using the time of travel (t) of the wave 27 through the blood pool that has a known density. In addition, the reflected wave 28 signal is used by the imaging circuitry 26c to generate an image 4 that is displayed on a screen or monitor 28. This frame 29 of the image 4 is typically relatively small (on the order of a few millimeters by a few millimeters) due to the size of the ultrasonic transducer 25 (i.e. the diameter and arrangement of the crystals in the transducer 25) which must be of a small scale to be used in intracardiac applications.

To aid the user in interpreting the ultrasound image 4, the present system 1 employs a catheter navigation system 3 as illustrated in FIGS. 1 and 2. This navigation system 3 determines the location in space and the orientation of the catheter distal end 16 and is thereby able to highlight or indicate on a context map 6 what portion of the heart wall 21 is displayed in the ultrasound image 4. Read together, the ultrasound image 4 and the highlighted context map 6 give the user information to position the catheter 12 in a desired location to view pertinent areas of the heart 5. In addition, the coordination of the image 4 and the highlighted context map 6 allow the user to manipulate the catheter to sequentially capture a number of image frames to generate a geometry of a larger portion of the heart or of the whole heart.

Various techniques have been proposed to carry out measurements of catheter location. Although the various techniques differ in detail, most systems involve the generation of a non-ionizing field in the heart and the detection of a catheter element within the field. The source of the field may be exterior of the patient or may be created within the heart itself with an appropriate catheter system. However, all of these techniques generate a set of points having locations in physical space. Suitable techniques are known from the incorporate references and U.S. Pat. No. 5,697,377 to Wittkampf. A generated field creates a detectable signal at a sensor element on the catheter. The nature of the field dictates the sensor element. Electrical fields may be detected by electrodes, while magnetic fields may be detected by magnetic sensors.

In greater detail, the illustrated embodiment of a catheter navigation system 3 includes a sensor electrode array 35 proximate the distal end 16 of the catheter tube 15. The electrode array 35 preferably includes a small collection of spaced sensor electrodes 40, 42, 44, 46, 48, that are deployed such that they are spaced from one another sufficiently to yield accurate position and orientation data when exposed to orthogonal currents as taught by Wittkampf. An example of an electrode array 35 configuration that achieves this objective is that disclosed by Desai in the patents discussed above, and incorporated herein by reference, in the Background section. The Desai configuration is illustrated in FIGS. 3A-3C. and is characterized by a plurality of side sensor electrodes 42, 44, 46, 48 equally spaced around the distal end 16 of a tubular catheter 15. A further, central electrode 40 is fixed to the distal end 16 on the catheter axis 50. The four side electrodes 42, 44, 46, 48 lie in the same plane 52 (FIG. 2) and are equally spaced from adjacent electrodes. The side electrodes 42, 44, 46, 48 are at the apexes of a square pattern with the central electrode 40 in the center of the square. The electrodes may be made of highly electrically conductive material. A plurality of longitudinally directed slits, as exemplified by slits 55 and 56, are cut through the tube 15 from a point adjacent to the terminating end 60 to a distance away from the terminating end 60. The slits 55, 56 define and form intermediate limbs 62, 63, 64, 65. The electrodes 42, 44, 46, 48 are positioned with one electrode to a limb 62, 63, 64 or 65. By applying a compressive force to the end 60, the limbs 62-65 buckle, thereby spreading the side electrodes 42, 44, 46, 48 apart, as illustrated in FIG. 3C.

Alternative electrode arrangements are contemplated. An arrangement with at least two electrodes can provide position and orientation data, though increasing the number and spacing of electrodes yields a higher degree of accuracy.

FIG. 1 illustrates additional elements of the navigation system 3. External patch electrodes 70, 71, 72, 73 are placed on the patient, directed substantially near the heart. The electrodes 70-73 are electrically connected to navigation circuitry 80 which imparts controlled current in a desired fashion to the electrodes 70-73. The navigation circuitry 80 is also electronically connected to the sensor electrodes 40, 42, 44, 46, 48 (as depicted by arrow 75) and receives and processes signals from the sensing electrodes 40, 42, 44, 46, 48.

According to the techniques described by Wittkampf in the patents noted above in the Background section and incorporated herein by reference, the navigation circuitry 80 imparts orthogonal current signals through the patient. Each of the signals has a respective characteristic that renders it distinguishable from the other orthogonal signals. In response to the field generated by this current, the sensing electrodes 40, 42, 44, 46, 48 send voltage signals to the navigation circuitry 80. The navigation circuitry 80 processes this signal information in the manner described in pending U.S. patent application Ser. No. 10/819,027 to determine the location of the catheter distal end 16, as well as the orientation of the catheter tube 15 as defined by the vector "R" (FIG. 2) extending axially from the end 16 of the catheter tube 15.

In a preferred embodiment the navigation circuitry 80 is linked for data transfer (as depicted by arrow 82) to a computer system 90 having a user interface to allow control of the navigation circuitry. In addition, in a preferred embodiment, the ultrasound processor 26 is linked for data transfer (as depicted by arrow 92) to a computer system 90 having a user interface to allow control of the ultrasound processor. Most preferably, the navigation circuitry 80 and the ultrasound processor are linked to a single computer that coordinates the operation of the imaging being done by the ultrasound system 2 with the navigation system 3.

The navigation circuitry 80 is linked for data transfer (as depicted by arrow 94) to a display screen or monitor 100. Similarly, the ultrasound processor 26 is linked for data transfer (as depicted by arrow 96) to a screen or monitor 102. The navigation circuitry 90 generates a context map 6 of the whole heart 5 or of a relatively large section of the heart 5 with an indication thereon of the location of the catheter distal end 16. More specifically, the computer system 90, with processing capabilities, coordinates the position and orientation data from the navigation system 3 with the distance-to-wall data received from the ultrasound system 2 to compute and illustrate, on monitor 100, the location on the heart of the frame 4 that is simultaneously displayed on an ultrasound image display screen or monitor 102. In this manner, the highlighted or animated region 105 of the context map 6 depicts the portion or frame of the heart wall at which the ultrasound is "pointed". In one embodiment, monitors 100 and 102 are separate screens; in alternate embodiments, both images (the context map 6 and the ultrasound image 4) are depicted on one monitor. The process of capturing ultrasound data and making the locating calculations occurs fast enough that the distance data can be used to computer motion data if desired.

Figure 4A:
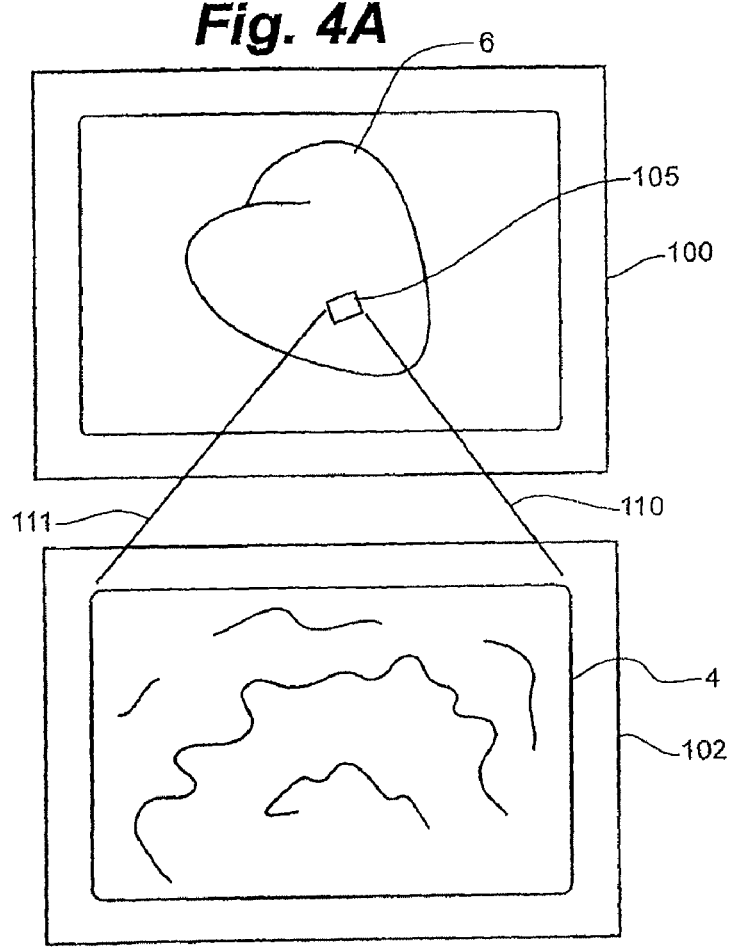
FIG. 4a is a schematic illustration of an image of heart geometry and an ultrasonic image generated by the system 1 taken at a first frame.

FIG. 4 further illustrates the relationship between the context map 6 and the ultrasound image frame 4: the highlighted region 105 of the context map 6 indicates the location in the heart of the ultrasound image frame 4. The context map 6 presents a wider field of view than is shown by the ultrasound image frame 4, and the context map 6 includes the frame 4 shown by the ultrasound image. This relationship between the relatively small field of view shown by the ultrasound frame 4 and the relatively larger field of view (including the frame 4) shown by the context map 6 is suggested by projection lines 110, 111.

Figure 5B:
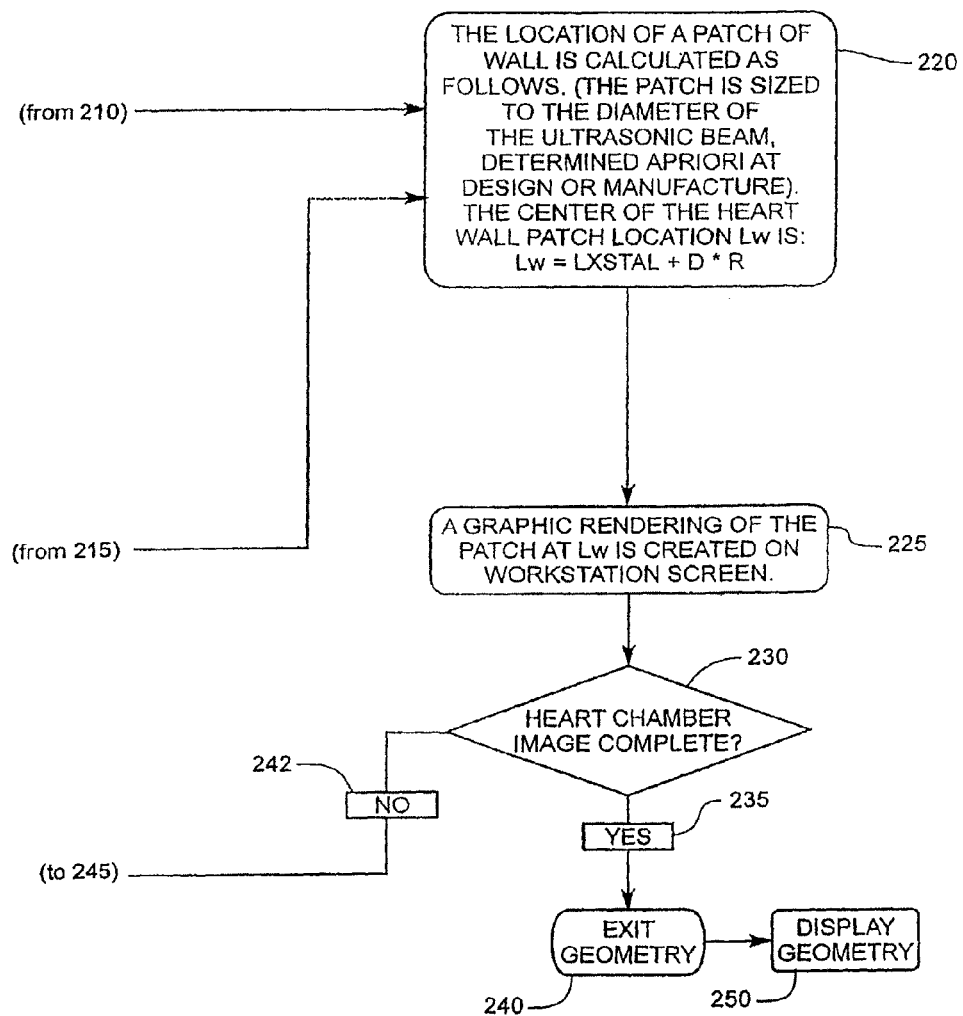
FIG. 5 is a flow chart depicted a method of using the system of FIG. 1 to generate a geometry of the heart.

The system 1 can be used to generate a geometry of the heart through iterative ultrasound imaging made feasible through the manipulation of the catheter system 10 using the navigation system 3 for guidance. FIG. 5 is a flow chart depicting the steps in the iterative process 200. The user positions (205) the catheter system 10 in the chamber of the heart 5. As depicted in step 210, electric potentials are applied to electrodes 70-73 and this potential is sensed by electrodes 40, 42, 44, 46, 48. Using Wittkampfs method, the 3D positions of each sense electrode 40, 42, 44, 46, 48 are determined and displayed. In addition, an orientation vector R is determined. Because the ultrasound crystal is in a known fixed location in relation to the catheter head 60, the location (Lxtal) of the ultrasound crystal is determined.

At essentially the same time, the ultrasound system 2 emits and senses a sound wave. The distance D to the heart wall 21 is calculated as D=Vb*t, where Vb is the apriori known velocity of the ultrasound signal in blood and t is the time measured from issuing the pulse to sensing the returned echo 28. This ultrasound process is indicated by block 215.

Applying the position data from step 210 and the ultrasound data from step 215, the location of a frame or patch 4 of the wall is calculated (220). The ultrasound data is stored in association with the location and orientation data. The location Lw of the center of the patch or frame 4 is calculated as follows: Lw=Lxstal+D*R. This location is located in relation to the catheter (Lw); in addition, the x, y, z coordinates of the wall patch in space can be calculated and stored, since the 3D position and orientation of the transducer 25 is known, along with the distance D to the wall.

A graphic rendering 105 of the patch or frame 4 is created (225) on a screen or monitor 100.

As indicated by decision block 230, if the view of the single frame 4 is sufficient for the user's purposes (235), the process may end here (240). However, if the user has not viewed the site of interest in full (242), the user may, based upon the graphic image in the context map 6, "build" a geometry of a larger portion of the heart, or of the whole heart, by iteratively or sequentially imaging different frames (which may or may not overlap) of the heart, with the system 1 collecting and storing position and orientation data in association with the ultrasound data for each such frame. To move from frame to frame, the user manipulates the catheter system 10 to change the orientation R of the catheter system 10 or to move the catheter system 10 to a new position within the heart 5, such that the ultrasound system "points at" and displays a different frame or patch 4'. This repositioning step is indicated at reference number 245. Thereafter, the position determining step 210, the ultrasound step 215, the calculation step 220 and the graphic rendering step 225 and the decision step 230 are repeated until the resulting geometry of the heart is sufficient (235) for the user's purposes. The completed geometry is displayed (250). Positioning and orientation of the catheter system 10 may be accomplished manually. Alternatively, the catheter system is coupled to a robotic mechanism controlled, for example, by the computer 90, to position and orient the catheter.

Figure 4B:
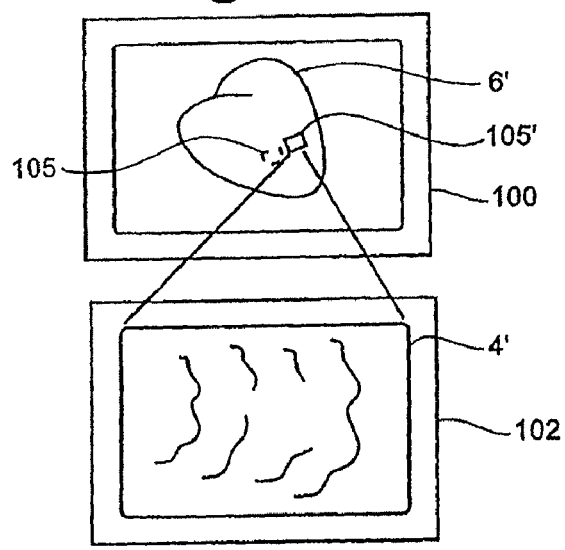
FIG. 4b is a schematic illustration of an image of heart geometry and an ultrasonic image generated by the system 1 taken at a second frame.

FIG. 4b shows the how the context map 6' appears with the ultrasound system 2 trained on a second patch or frame 105'. The first frame 105 is indicated for reference with broken lines in the drawing of FIG. 4b; it may or may not be indicated in some manner on the context map 6' shown on the monitor 100. FIG. 4b also shows the relationship between the frame 105' on the context map 6' to the ultrasound frame 4' shown on the ultrasound image monitor 102.

The system 1 of the present invention offers advantage over traditional ICE, where a large number of crystals in the transducer are necessary to achieve the desired image quality, because with the present invention allows for a smaller number of crystals to achieve a comparable level of performance, because it has the ability to signal average the acquired data. This is possible because the ultrasound data is acquired from a known location. Combining this knowledge with cardiac gating, multiple acquisitions from a site may be averaged.

Another advantage of the present invention with a smaller number of crystals over traditional ICE is that the head of the catheter may be forward-looking, i.e. the wave 27 propagated by the transducer 25 travels in a direction R that is generally parallel to the axis 50 of the catheter 10. Traditional ICE catheters, like those shown by Seward, "look" off to the side of the catheter and therefore are somewhat more difficult to operate.

Yet another advantage is that the catheter system 10, having a customary size and flexibility and being equipped with electrodes, may be used as a standard cardiac electrophysiology mapping catheter.

Although an illustrative version of the device is shown, it should be clear that many modifications to the device may be made without departing from the scope of the invention.

What is claimed is:

1. A system for navigating an ultrasound catheter to image a beating heart, comprising:
   a catheter carrying an ultrasonic transducer configured to generate a sound wave and sense an echo wave to obtain ultrasound data for a first portion of the interior surface of the heart and a sensor element configured to generate a signal indicative of a position of the first portion; and,
   an imaging system for simultaneously displaying an ultrasound image of the first portion and a three-dimensional context map of the heart and simultaneously highlighting a first surface on the context map corresponding to the first portion and a second surface on the context map corresponding to a second portion of the interior surface of the heart for which ultrasound data was previously captured by the ultrasonic transducer.

2. The system of claim 1 wherein the imaging system displays the ultrasound image in real time.

3. The system of claim 1 wherein the first and second portions partially overlap.

4. The system of claim 1 wherein the context map displays a section of the heart that includes the first portion and additional portions of the heart adjacent the first portion.

5. The system of claim 1, further comprising a robotic mechanism operatively coupled to the catheter to position and orient the catheter.

6. The system of claim 1 wherein the position of the first portion is determined responsive to a position of the sensor element and the ultrasound data.

7. A system for navigating an ultrasound catheter to image a beating heart, comprising:
   a catheter carrying a sensor element and an ultrasonic transducer configured to generate a sound wave and sense an echo wave to obtain ultrasound data for a first portion of the interior surface of the heart;
   a navigation system operatively coupled to the sensor element for determining a position of the first portion; and,
   an imaging system for simultaneously displaying an ultrasound image of the first portion and a three-dimensional context map of the heart and simultaneously highlighting a first surface on the context map corresponding to the first portion and a second surface on the context map corresponding to a second portion of the interior surface of the heart for which ultrasound data was previously captured by the ultrasonic transducer.

8. The system of claim 7, wherein said navigation system determines a position and an orientation of the sensor element.

9. The system of claim 7 wherein said sensor element is disposed on a longitudinal axis of the catheter and the catheter includes a plurality of additional sensor elements, each one of the additional sensor elements spaced radially from the axis and at approximately equal circumferential distances from circumferentially adjacent others of the additional sensor elements.

10. The system of claim 7 wherein said additional sensor elements are in a common plane.

11. The system of claim 7 wherein the imaging system displays the ultrasound image in real time.

12. The system of claim 7 wherein the first and second portions partially overlap.

13. The system of claim 7 wherein the context map displays a section of the heart that includes the first portion and additional portions of the heart adjacent the first portion.

14. The system of claim 7, further comprising a robotic mechanism operatively coupled to the catheter to position and orient the catheter.

15. A method of navigating an ultrasound catheter to image a beating heart, comprising the steps of:
   positioning a catheter in the interior of the heart, the catheter carrying an ultrasonic transducer and a sensor element;
   determining a position of the sensor element;
   generating a sound wave and sensing an echo wave to obtain ultrasound data for a first portion of the interior surface of the heart; and,
   simultaneously displaying an ultrasound image of the first portion and a three-dimensional context map of the heart and simultaneously highlighting a first surface on the context map corresponding to the first portion and a second surface on the context map corresponding to a second portion on the interior surface of the heart for which ultrasound data was previously captured by the ultrasonic transducer.

16. The method of claim 15, further comprising the steps of:
   determining a position of the ultrasonic transducer responsive to the position of the sensor element;
   calculating a distance from the ultrasonic transducer to the first portion; and,
   determining a location of the first portion responsive to the position of the ultrasonic transducer and the distance.

17. The method of claim 15, further comprising the steps of:
   repositioning the catheter in the interior of the heart;
   generating a sound wave and sensing an echo wave to obtain ultrasound data for a third portion of the interior surface of the heart; and,
   simultaneously displaying an ultrasound image of the third portion and a three-dimensional context map of the heart and simultaneously highlighting the first and second surfaces and a third surface on the context map corresponding to the third portion.

18. The method of claim 15 wherein the ultrasound image is displayed in real time.

19. The method of claim 15 wherein the first and second portions partially overlap.

* * * * *